(12) United States Patent
Marenco

(10) Patent No.: US 11,577,019 B2
(45) Date of Patent: Feb. 14, 2023

(54) ADMINISTRATION OF A VACCINE OR EMERGENCY ADMINISTRATION OF A MEDICAMENT USING A DENTAL CARPULE

(71) Applicant: Ken Marenco, Ottawa (CA)

(72) Inventor: Ken Marenco, Ottawa (CA)

( * ) Notice: Subject to any disclaimer, the term of this patent is extended or adjusted under 35 U.S.C. 154(b) by 289 days.

(21) Appl. No.: 17/060,983

(22) Filed: Oct. 1, 2020

(65) Prior Publication Data
US 2022/0105259 A1    Apr. 7, 2022

(51) Int. Cl.
| | | |
|---|---|---|
| A61M 5/00 | (2006.01) | |
| A61M 5/24 | (2006.01) | |
| A61M 5/31 | (2006.01) | |
| A61M 5/32 | (2006.01) | |
| A61J 1/06 | (2006.01) | |
| A61J 1/20 | (2006.01) | |
| A61J 1/14 | (2023.01) | |
| A61M 5/315 | (2006.01) | |

(52) U.S. Cl.
CPC .............. *A61M 5/002* (2013.01); *A61J 1/062* (2013.01); *A61J 1/1406* (2013.01); *A61J 1/20* (2013.01); *A61M 5/2455* (2013.01); *A61M 5/3129* (2013.01); *A61M 5/31593* (2013.01); *A61M 5/3202* (2013.01); *A61M 2210/0625* (2013.01)

(58) Field of Classification Search
CPC .......... A61M 5/002; A61M 2210/0625; A61M 5/28; A61J 1/062
See application file for complete search history.

(56) References Cited

U.S. PATENT DOCUMENTS

| | | | |
|---|---|---|---|
| 4,919,657 A * | 4/1990 | Haber ..................... | A61M 5/24 604/234 |
| 7,488,305 B2 | 2/2009 | Mickley et al. | |
| 8,827,963 B2 | 9/2014 | Hirschel et al. | |
| 9,055,992 B2 | 6/2015 | Larson | |
| 10,195,267 B2 | 2/2019 | Knolle et al. | |
| 10,279,102 B2 | 5/2019 | Kavallar et al. | |
| 10,279,114 B2 | 5/2019 | Latiolais | |
| 2006/0216245 A1* | 9/2006 | Haraguchi ............. | A61P 23/02 514/649 |
| 2015/0342986 A1* | 12/2015 | Abrahmsohn .......... | A61P 23/02 424/678 |
| 2018/0147357 A1 | 5/2018 | Marashi et al. | |
| 2019/0083199 A1* | 3/2019 | Cassinis ................ | A61B 50/36 |

* cited by examiner

*Primary Examiner* — Bradley J Osinski

(57) ABSTRACT

An illustrated view of an exemplary emergency kit for use in an emergency medical condition and a method for automating the ordering of the emergency kits for dentist is presented. The emergency kit is useful for providing short-term medical relief in an emergency while waiting for ambulance or other emergency medical personnel to arrive at the scene. The emergency kit provides a useful medical syringe for use by a dentist in a mouth of a patient experiencing an emergency medical condition.

8 Claims, 3 Drawing Sheets

ADMINISTRATION OF A VACCINE OR EMERGENCY ADMINISTRATION OF A MEDICAMENT USING A DENTAL CARPULE

FIELD OF THE INVENTION

This invention relates to administering emergency medication. More particularly, it relates to utilization of a dental carpule for emergency administration of a medicant or vaccine.

BACKGROUND

A medical emergency kit can consist of several drugs, some of which come in multi-dose vials, uni-dose vials, preloaded auto-injector devices, pills and sprays. Epinephrine comes in auto-injector and multi-dose vials, uni-dose vials, etc.

At continuing education courses for medical emergencies in a dental office, the lecturers suggest that if a dentist encounters an emergency which calls for the injection of a multi-dose vial medication, such as epinephrine or diphenhydramine, use of a basic medical syringe may be necessary for drawing up the dose required. Muscle injections (such as in the leg or arm) are foreign for dentists as the dentist is accustomed to injecting in the mouth of the patient. The mouth of the patient is most likely already anaesthetized at this point, but the muscle in the leg or arm is the target suggested by the lecturers.

Further, to be prepared for the emergency, the dentist must order yearly or later, the multidose or unidose vials and the medical syringes if they have expired. The multidose vials and syringes are items never used for any other purpose by the dentist except for than in an emergency. Making sure all items are stocked, not expired or too old, requires office protocols and a staff member in charge of the protocol. In small dental offices, the dentist usually tends to this protocol, however in larger dental offices staff must be utilized to perform this protocol.

When this protocol is being tended to by staff, the dentist must trust that the protocols are being followed and the emergency kit is always properly stocked with unexpired drugs and equipment. In most cases a prescription has to be filed, faxed and picked up, although delivery of the emergency kit is provided in some cases.

DETAILED DESCRIPTION

Figure 1:
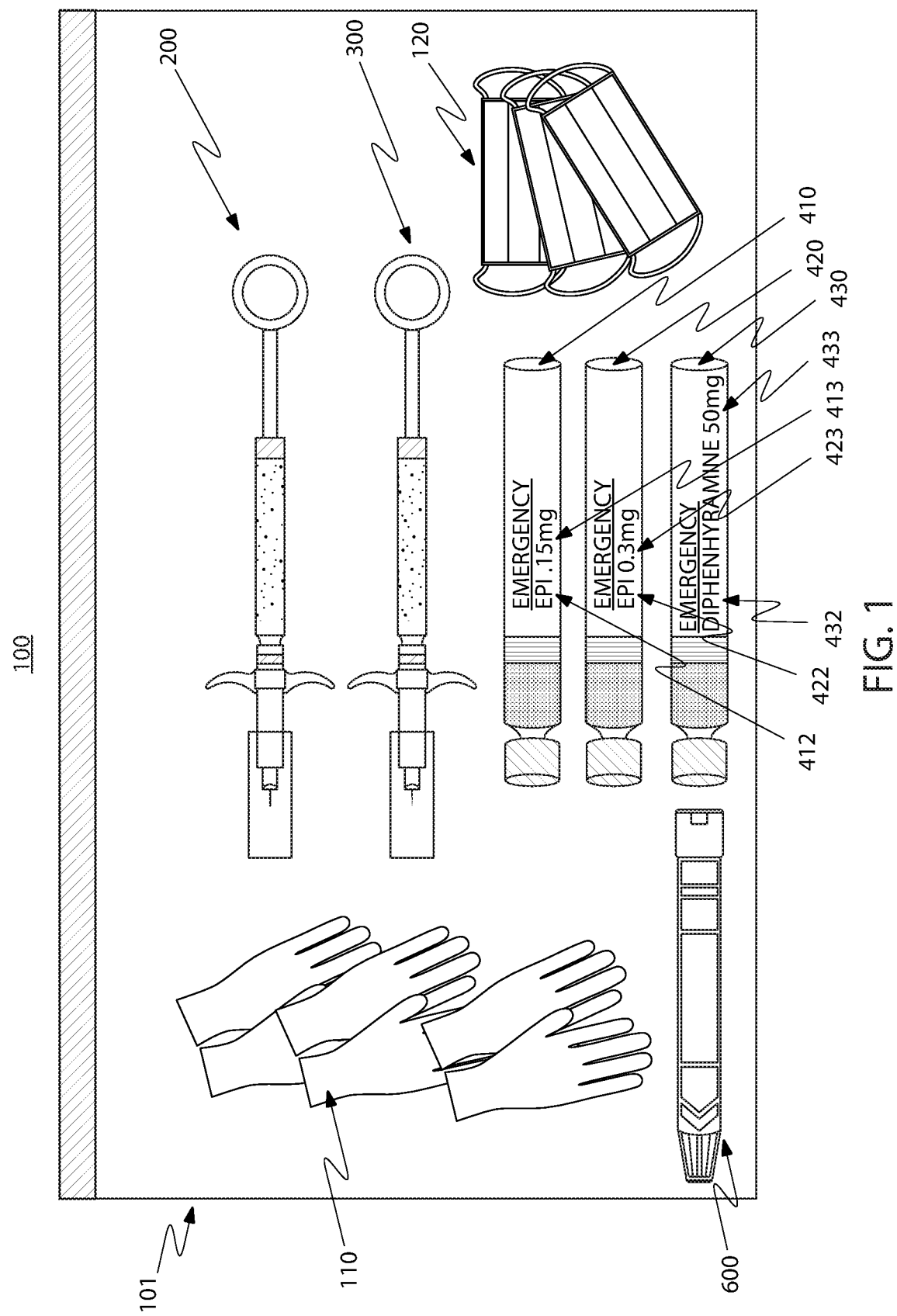
FIG. 1 is an illustrated view of an exemplary emergency kit.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. Such terms do not generally signify a closed list.

"Above," "adhesive," "affixing," "any," "around," "both," "bottom," "by," "comprising," "consistent," "customized," "enclosing," "friction," "in," "labeled," "lower," "magnetic," "marked," "new," "nominal," "not," "of," "other," "outside," "outwardly," "particular," "permanently," "preventing," "raised," "respectively," "reversibly," "round," "square," "substantial," "supporting," "surrounded," "surrounding," "threaded," "to," "top," "using," "wherein," "with," or other such descriptors herein are used in their normal yes-or-no sense, not as terms of degree, unless context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

Referring to FIG. 1, an illustrated view of an exemplary emergency kit 100 for use in an emergency medical condition is presented. The emergency kit 100 is useful for providing short-term medical relief in an emergency while waiting for ambulance or other emergency medical personnel to arrive at the scene. The emergency kit 100 provides a useful medical syringe for use by a dentist in a mouth of a patient experiencing an emergency medical condition.

The emergency kit 100 may include a plurality of gloves 110, a plurality of masks 120, a first prefilled syringe 200, a second prefilled syringe 300 and one or more additional carpules 410, 420, 430. Although the emergency kit 100 is shown in a container 101, the emergency kit 100 may be individually sent and the dentist would be required to determine how to carry the emergency kit 100 such as in a bag or other carrying article. In another embodiment, the syringe 200 used in the kit 100 may not be prefilled. It is therefore noted that the kit 100 may also be provided and configured for use with a reusable type syringe commonly used in a dental office. In a preferred embodiment, the kit 100 may also be configured without a syringe 200 and provided with the carpules 410, 420, and 430.

The first pre-filled syringe 200 is preferably prefilled for an adult dosage of a drug to be administered during an emergency. The second pre-filled syringe 300 is preferably prefilled for a child dosage of a drug to be administered during an emergency.

Each of the additional carpules 410, 420, 430 preferably contain a different drug or dosage of a drug. One of the carpules 410 may contain an adult dosage while another of the carpules 420 may contain a child dosage. A first of the carpules 410 has a first strength 412 of a first drug 413. The first drug 413 preferably being epinephrine. The first strength 412 preferably being 0.3 mg. More than one carpules 410 may be available and used for the adult dose. It is contemplated that up to four (4) of the first drugs 413 may be provided for used in some instances.

A second of the carpules 420 has a second strength 422 of a second drug 423. The second drug 423 preferably being epinephrine. The second strength 422 preferably being 0.15 mg. The second of the additional carpules 420 has a dosage sufficient for a child.

A third of the carpules 430 has a third strength 432 of a third drug 433. The third drug 433 preferably being diphenhydramine. The third strength preferably being 50 mg. In another embodiment, the third drug 433 may be provided in a 25 mg dose for a child.

Figure 2:
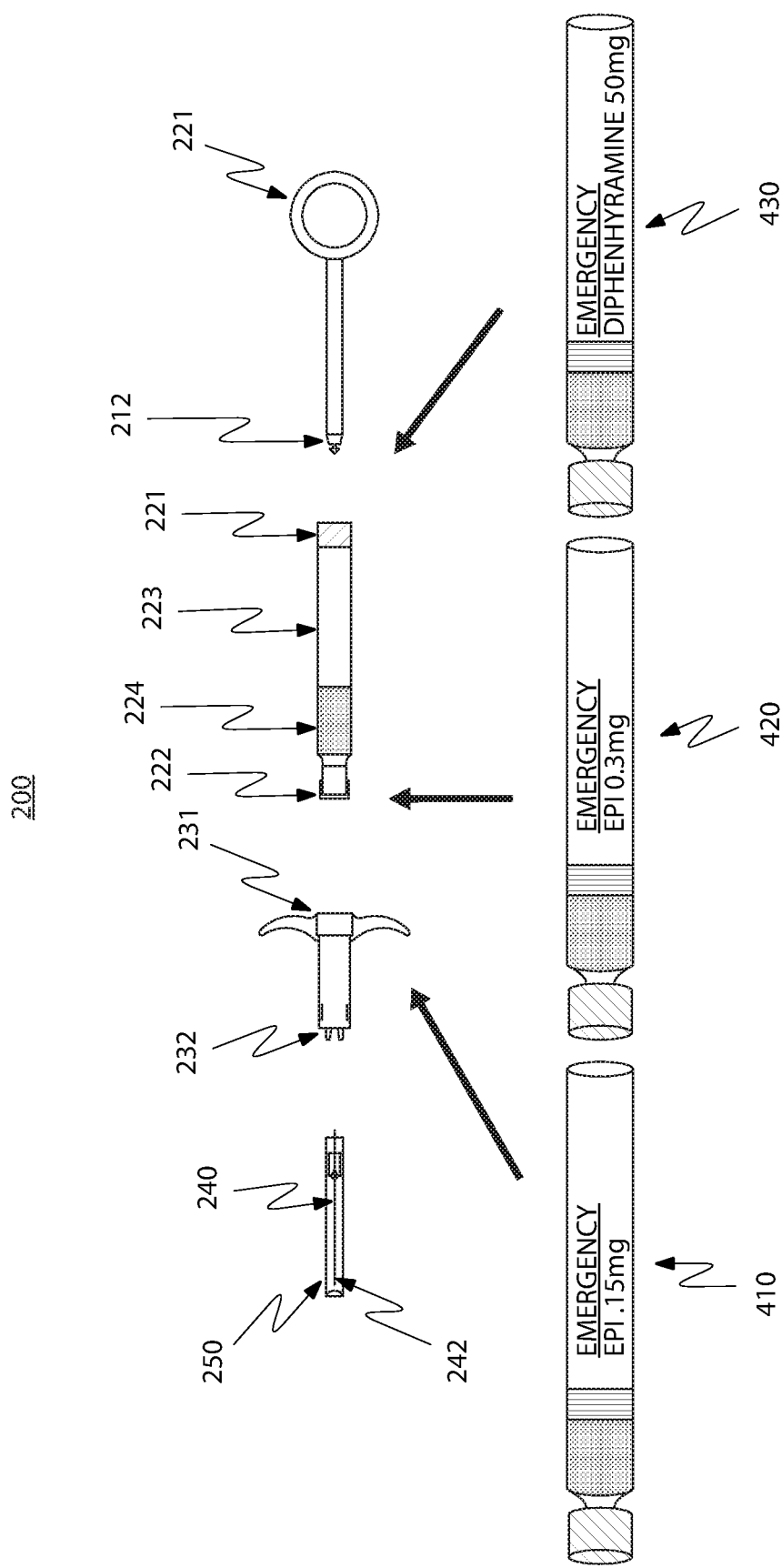
FIG. 2 is an illustrated view of an exemplary syringe for the emergency kit shown in FIG. 1.

Moving now to FIG. 2, an illustrated view of an exemplary syringe for the emergency kit shown in FIG. 1.

The syringe 200 has a plunger 210, a carpule 220, a barrel 230, a needle 240, an EpiPen® 600 and a needle cap 250. The Epipen 600 is first used and has an extended needle for use as is well known.

The plunger 210 has a top 211 and a bottom 212. The carpule 220 has a top 221, a bottom 222 and an interior 223. The interior 223 of the carpule 220 contains a drug 224. The drug 224 is preferably epinephrine, however other drugs or vaccines are hereby contemplated, including, but not limited to, diphenhydramine, etc. The carpule 410 chosen for the example is carpule 410 although carpule 420 carpule 430 may be used in a similar manner as determined by the age, weight, conditions of the patient.

The barrel 230 is preferably hollow however the barrel 230 has a first end 231 and a second end 232. The second end 232 is substantially closed except to allow for the needle 240 to be inserted thru the second end 232 of the barrel 230. The barrel 230 is configured to be side-loaded through an opening (not shown).

The needle case 250 is removably and securely coupled to the needle 240. The needle case 250 is removed prior to the use of the syringe 200. The needle has a first end 241 and a second end 242. The needle 240 is preferably twenty-five (25) gauge, however other sizes of needles are hereby contemplated, including, but not limited to, twenty-seven (27) gauge, thirty (30) gauge, etc. The smaller needle 240 is useful when inserting the needle 240 into a muscle in the mouth of the patient.

The carpule 220 is first inserted into the first end 231 of the barrel 230 until it rests at the bottom 222 of the barrel 230. The needle 240 is coupled to the second end 232 of the barrel 230. The needle 240 is inserted thru the second end 232 of the barrel 230 puncturing a hole and the needle be securely coupled to the interior (fluid-filled portion) 223 of the carpule 220.

The second end 212 of the plunger 210 is inserted into the first end 231 of the barrel 230 until the second end 212 of the plunger 210 becomes in contact with the top 221 of the carpule 220. The carpule 220 is premeasured and loaded.

The needle cap 250 is removed from the needle 240. The syringe 200 is then inserted into a mouth of a patient. The needle 240 is then directed into a muscle located in the mouth (or other suitable location such as the floor of the mouth) of the patient. The plunger 210 is pushed against the top 221 of the carpule 220 thereby ejecting the drug 224 in the interior 223 of the carpule 220 thru the needle 240 and into the muscle of the patient.

Figure 3:
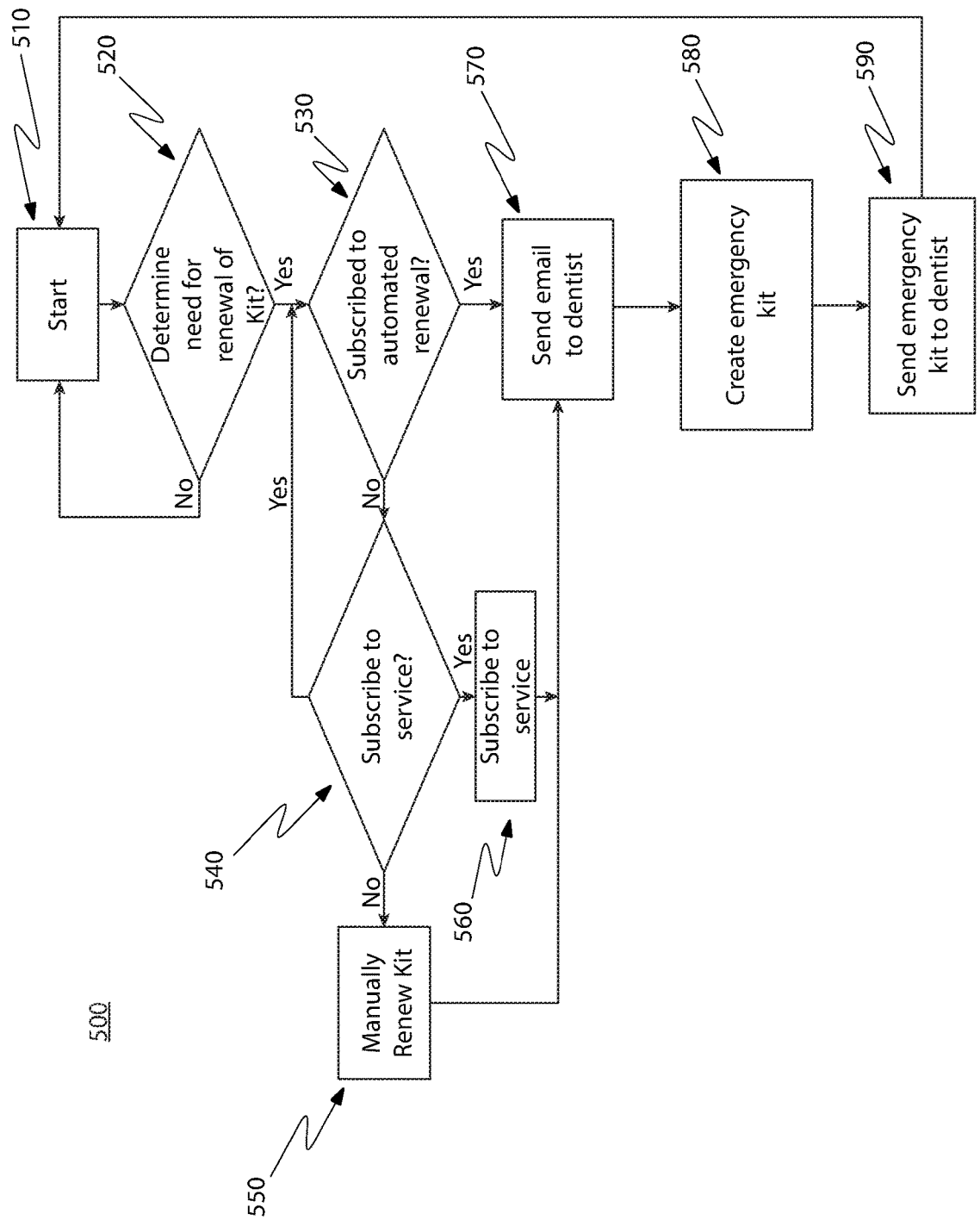
FIG. 3 is an illustrated view of a flow chart for fulfillment of the emergency kit shown in FIG. 1.

Referring now to FIG. 3, an illustrated view of a flow chart 500 for fulfillment of the emergency kit shown in FIG. 1.

The flow chart 500 begins at start 510. A determination to whether the emergency kit 100 needs to be renewed at 520 is made. The emergency kit 100 may need to be renewed for one or more of the following reasons, but not limited to: expiration of the drug 413, 423, 433, prior use of one of the syringes 200, 300, etc.

At 520, if the kit is determined to not in need of renewal, then the process stops and returns waiting to be started, at 510, at a later time. At 530 it is determined if the dentist is subscribed to automated renewal.

If at 530 the dentist is not subscribed to automated renewal, then it is determined at 540 whether the dentist desires to be subscribed to the automated renewal service. If, at 540, it is determined that the dentist does not desire to be subscribed, then a manual prescription is filed to obtain a new emergency kit at 550.

If, at 540 it is determined that the dentist does desire to be subscribed, then the paperwork is completed, including filing of a charge card, to subscribe to the automatic renewal system at 560.

At 570, after either manually renewing the kit at 550, subscribing to the automated service at 560 or having determined that the dentist is subscribed to the automated service at 530, an email is received by the dentist acknowledging the renewal and an expected date of delivery of the emergency kit 100.

Next, at 580, the emergency kit 100 is created and after it is created the emergency kit 100 is sent to the dentist at 590. The process returns to the start at 510 to wait for the next instance for use of the flowchart.

In the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The features described with respect to one embodiment may be applied to other embodiments or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for an emergency administration of a medicant using a dental carpule, the method comprising:
    obtaining a kit, the kit comprising:
        obtaining a plurality of gloves, the gloves being one or more sizes; obtaining a plurality of masks, the masks being one or more sizes; assembling a syringe, the syringe having a plunger, a carpule, a barrel, a
    needle and a needle cap; and
    one or more additional carpules, the one or more carpules having one or more drugs or vaccine, the syringe having a plunger, a carpule, a barrel, a needle and a needle cap the syringe having a plunger, a carpule, a barrel, a needle and a needle cap, the drug being diphenhydramine and epinephrine.

2. The method of claim 1, wherein a first of the drugs having a strength.

3. The method of claim 2, wherein the strength being 0.3 mg.

4. The method of claim 1, wherein the carpule being coupled into the barrel.

5. The method of claim 1, wherein the needle being inserted into a second side of the barrel and wherein the needle being coupled to an interior of the carpule.

6. The method of claim 1, wherein the plunger being inserted into the barrel and wherein the plunger being in contact with a top of the carpule.

7. The method of claim 1, wherein the syringe being inserted into a mouth of a patient, and wherein the needle being inserted into a muscle in the mouth of the patient.

8. The method of claim 1, wherein the syringe being inserted into a suitable location in the mouth of a patient, and wherein the needle being inserted into a muscle in the mouth of the patient.

* * * * *